United States Patent
Peel et al.

(10) Patent No.: US 11,918,581 B2
(45) Date of Patent: Mar. 5, 2024

(54) COMBINATION THERAPY COMPRISING JAK PATHWAY INHIBITOR AND ROCK INHIBITOR

(71) Applicant: Incyte Corporation, Wilmington, DE (US)

(72) Inventors: Michael Peel, Philadelphia, PA (US); Paul Smith, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/571,844

(22) Filed: Jan. 10, 2022

(65) Prior Publication Data

US 2022/0226327 A1 Jul. 21, 2022

Related U.S. Application Data

(60) Provisional application No. 63/253,384, filed on Oct. 7, 2021, provisional application No. 63/135,969, filed on Jan. 11, 2021.

(51) Int. Cl.
*A61K 31/519* (2006.01)
*A61K 31/517* (2006.01)
*A61P 37/06* (2006.01)

(52) U.S. Cl.
CPC .......... *A61K 31/519* (2013.01); *A61K 31/517* (2013.01); *A61P 37/06* (2018.01)

(58) Field of Classification Search
CPC ...... A61K 31/519; A61K 31/517; A61P 37/06
See application file for complete search history.

(56) References Cited

U.S. PATENT DOCUMENTS

| | | |
|---|---|---|
| 4,997,834 A | 3/1991 | Muro et al. |
| 6,140,333 A | 10/2000 | Tsuchiya et al. |
| 7,572,913 B2 | 8/2009 | McKarracher et al. |
| 7,598,257 B2 | 10/2009 | Rodgers et al. |
| 8,415,362 B2 | 4/2013 | Rodgers et al. |
| 8,722,693 B2 | 5/2014 | Rodgers et al. |
| 9,249,149 B2 | 2/2016 | Silverman et al. |
| 9,540,367 B2 | 1/2017 | Tung |
| 9,655,854 B2 | 5/2017 | Yeleswaram et al. |
| 9,815,820 B2 | 11/2017 | Poyurovsky et al. |
| 10,561,616 B2 | 2/2020 | Yeleswaram et al. |
| 2010/0298334 A1 | 11/2010 | Rodgers et al. |
| 2011/0059951 A1 | 3/2011 | Rodgers et al. |
| 2011/0224190 A1 | 9/2011 | Huang et al. |
| 2012/0149681 A1 | 6/2012 | Rodgers et al. |
| 2012/0149682 A1 | 6/2012 | Rodgers et al. |
| 2013/0018034 A1 | 1/2013 | Yao et al. |
| 2013/0045963 A1 | 2/2013 | Rodgers et al. |
| 2013/0060026 A1 | 3/2013 | Zhou et al. |
| 2014/0005166 A1 | 1/2014 | Rodgers et al. |
| 2014/0121198 A1 | 5/2014 | Li et al. |
| 2014/0256941 A1 | 9/2014 | Liu et al. |
| 2014/0343030 A1 | 11/2014 | Li et al. |
| 2015/0065484 A1 | 5/2015 | Yeleswaram et al. |
| 2015/0344497 A1 | 12/2015 | Zhou et al. |

FOREIGN PATENT DOCUMENTS

| | | |
|---|---|---|
| WO | WO 97/23222 | 7/1997 |
| WO | WO 98/06433 | 2/1998 |
| WO | WO 99/64011 | 12/1999 |
| WO | WO 00/09162 | 2/2000 |
| WO | WO 01/56988 | 8/2001 |
| WO | WO 2002/000196 | 1/2002 |
| WO | WO 02/076976 | 10/2002 |
| WO | WO 02/076977 | 10/2002 |
| WO | WO 02/100833 | 12/2002 |
| WO | WO 2006/068208 | 6/2006 |
| WO | WO 2010/126626 | 11/2010 |

OTHER PUBLICATIONS

Hill, et al., New and Emerging Therapies for Acute and Chronic Graft Versus Host Disease, Therapeutic Advances in Hematology, vol. 9, No. 1, pp. 21-46 (2017). (Year: 2017).*
Berge et al., "Pharmaceutical Salts," J Pharm Sci., 1977, 66:1-19.
Boehler and Estenne, "Post-transplant bronchiolitis obliterans," Eur Respir J., 2003, 22:1007-1018.
Clinicaltrials.gov, "A Study of Itacitinib for the Prevention of Cytokine Release Syndrome Induced by Immune Effector Cell Therapy," NCT04071366, last updated May 27, 2022 [retrieved Sep. 19, 2022], retrieved from URL <https://www.clinicaltrials.gov/ct2/show/NCT04071366>, 10 pages.
Cooke et al, "The Biology of Chronic Graft-versus-Host Disease: A Task Force Report from the National Institutes of Health Consensus Development Project on Criteria for Clinical Trials in Chronic Graft-versus-Host Disease," Biol Blood Marrow Transplant., 2017, 23:211-234.
Cutler et al., "Belumosudil for Chronic Graft-Versus-Host Disease (cGVHD) after 2 or More Prior Lines of Therapy: The Rockstar Study (KD025-213)," Blood, Nov. 5, 2020, 136(Suppl 1):45-46.
Flynn et al., "Targeted Rho-associated kinase 2 inhibition suppresses murine and human chronic GVHD through a Stat3-dependent mechanism," Blood, Apr. 28, 2016, 127(17):2144-2154.
Fonesca et al., "Interleukin-6 as a key player in systemic inflammation and joint destruction," Autoimmunity Reviews, 2009, 8:538-542.
Fukami et al., "An obligatory role for lung infiltrating B cells in the immunopathogenesis of obliterative airway disease induced by antibodies to MHC class I molecules," Am J Transplant., 2012, 12:867-876.
Giralt et al., "Belumosudil shows promise for chronic GVHD," Healio, Dec. 6, 2022[retrieved on Mar. 29, 2022], retrieved from URL <https://www.healio.com/news/hematology-oncology/20201206/belumosudil-shows- promise-for-chronic-gvhd>, 3 pages.

(Continued)

*Primary Examiner* — Erich A Leeser
(74) *Attorney, Agent, or Firm* — Fish & Richardson P.C.

(57) ABSTRACT

The present application provides combination therapies comprising a JAK inhibitor and a ROCK inhibitor, and methods of using the same to treat disorders such as graft versus host disease (GVHD), restrictive allograft syndrome (RAS), chronic lung allograft dysfunction (CLAD), and systemic sclerosis (scleroderma).

22 Claims, 4 Drawing Sheets

(56) References Cited

OTHER PUBLICATIONS

Gupta et al., "IL-17A Blockade Attenuates Obliterative Bronchiolitis and IFN-gCellular Immune Response in Lung Allografts," Am J Respir Cell Mol Biol., 2017, 56(6):708-715.

Guschin et al., "A major role for the protein tyrosine kinase JAK1 in the JAK/STAT signal transduction pathway in response to interleukin-6," Embo J., 1995, 14:1421-1429.

Hill et al., "New and emerging therapies for acute and chronic graft 32 versus host disease, " Therap Adv Heamatol., Nov. 28, 2017, 9(1):21-46.

Hodge et al., "Bronchiolitis obliterans syndrome is associated with increased peripheral blood natural killer and natural killer T-like granzymes, perforin, and T-helper-type 1 pro-inflammatory cytokines," J Heart Lung Transplant., 2012, 31:888-895.

International Search Report and Written Opinion in International Application No. PCT/US2022/011756, dated Apr. 8, 2022, 15 pages.

Ishizaki et al., "Pharmacological Properties of Y-27632, a Specific Inhibitor of Rho-Associated Kinases," Mol Pharmacol., 2000, 57(5):976-983.

Kast et al., "Cardiovascular effects of a novel potent and highly selective azaindole-based inhibitor of Rho-kinase," Brit J Pharmacol., 2007, 152:1070-1080.

Leonard et al., "Dendritic cells and macrophages in lung allografts: A role in chronic rejection?," Am J Respir Crit Care Med., 2000, 161:1349-1354.

Meyer et al., "An international ISHLT/ATS/ERS clinical practice guideline: diagnosis and management of bronchiolitis obliterans syndrome," Eur Respir J., 2014, 44:1479-1503.

Park et al., "Homogeneous proximity tyrosine kinase assays: scintillation proximity assay versus homogeneous time-resolved fluorescence," Analytical Biochemistry, 1999, 269:94-104.

Philit et al., "Post-transplant obstructive lung disease ("bronchiolitis obliterans"): a clinical comparative study of bone marrow and lung transplant patients," Eur Respir J., 1995, 8:551-558.

Ravin, "Preformulation," Remington's Pharmaceutical Sciences, 17th Ed., Mack Publishing Company, Easton, 1985, p. 1418.

Schoettler et al., "Ruxolitinib is an effective steroid sparing agent in children with steroid refractory/dependent bronchiolitis obliterans syndrome after allogenic hematopoietic cell transplantation," Bone Marrow Transplantation, 2019, 54:1158-1160.

Scott et al., "Jaks, STATs, Cytokines, and Sepsis," Clin Diagn Lab Immunol., 2002, 9(6):1153-1159.

Smolen et al., "Effect of interleukin-6 receptor inhibition with tocilizumab in patients with rheumatoid arthritis (OPTION study): a double-blind, placebo-controlled, randomised trial," The Lancet, 2008, 371:987-997.

Zhao et al., "Efficacy and Safety of Fasudil in Patients With Subarachnoid Hemorrhage: Final Results of a Randomized Trial of Fasudil Versus Nimodipine," Neurol Med Chir(Tokyo)., 2011, 51:679-683.

\* cited by examiner

COMBINATION THERAPY COMPRISING JAK PATHWAY INHIBITOR AND ROCK INHIBITOR

TECHNICAL FIELD

Disclosed herein are combination therapies comprising a JAK pathway inhibitor and a ROCK pathway inhibitor, and methods of using the same to treat disorders such as graft versus host disease (GVHD), restrictive allograft syndrome (RAS), chronic lung allograft dysfunction (CLAD), and systemic sclerosis (scleroderma).

BACKGROUND

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. The Janus kinase family of protein tyrosine kinases (JAKs) belong to the non-receptor type of tyrosine kinases and include family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2).

The pathway involving JAKs and Signal Transducers and Activators of Transcription (STATs) is engaged in the signaling of a wide range of cytokines. Cytokines are low-molecular weight polypeptides or glycoproteins that stimulate biological responses in virtually all cell types. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "Jaks, STATs, Cytokines, and Sepsis." Clin Diagn Lab Immunol 9(6): 1153-9).

The JAK family plays a role in the cytokine-dependent regulation of proliferation and function of cells involved in immune response. The JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. Moreover, multiple cytokines that signal through JAK kinases have been linked to inflammatory diseases or conditions of the upper respiratory tract such as those affecting the nose and sinuses (e.g., rhinitis, sinusitis) whether classically allergic reactions or not. The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

Blocking signal transduction at the level of the JAK kinases holds promise for developing treatments for human cancers. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, selective JAK1 inhibitor itacitinib, {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, is reported in U.S. Pat. App. Pub. Nos. 2011/0224190 and 2015/0065484; and JAK1/2 inhibitor ruxolitinib, also known as (R)-3-(4-(7H-pyrrolo[2,3-d]pyrimidin-4-yl)-1H-pyrazol-1-yl)-3-cyclopentylpropanenitrile and INCB018424, which is sold as the phosphate salt under the trade names JAKAFI® and JAKAVI®, is reported in U.S. Pat. Nos. 7,598,257, 8,415,362, and 8,722,693, the disclosures of which are each incorporated herein by reference.

The Rho-associated coiled-coil kinase family members, consisting of Rho-associated kinase 1 (ROCK1) and Rho-associated kinase 2 (ROCK2), are serine-threonine kinases that are activated by Rho GTPases. Rho-associated kinase are involved in a wide range of cellular processes including inflammation (see e.g., Flynn, R., *Blood*, 2016, 127(17), 2144-54). While the two ROCK isoforms are similar, are differentially expressed and regulated in specific tissues. For example, ROCK1 is ubiquitously expressed at relatively high levels, whereas ROCK2 is preferentially expressed in cardiac and brain and skeletal muscle. The isoforms are also expressed in some tissues and in a developmental stage specific manner.

SUMMARY

The present application provides, inter alia, methods of treating a disease or disorder selected from graft versus host disease (GVHD), restrictive allograft syndrome (RAS), chronic lung allograft dysfunction (CLAD), and systemic sclerosis (scleroderma) in a subject, comprising administering to the subject:

(i) a Janus kinase (JAK) inhibitor; and
(ii) a Rho-associated protein kinase (ROCK) inhibitor.

Other features, objects, and advantages of the invention will be apparent from the description and from the claims.

DETAILED DESCRIPTION

Figure 1:
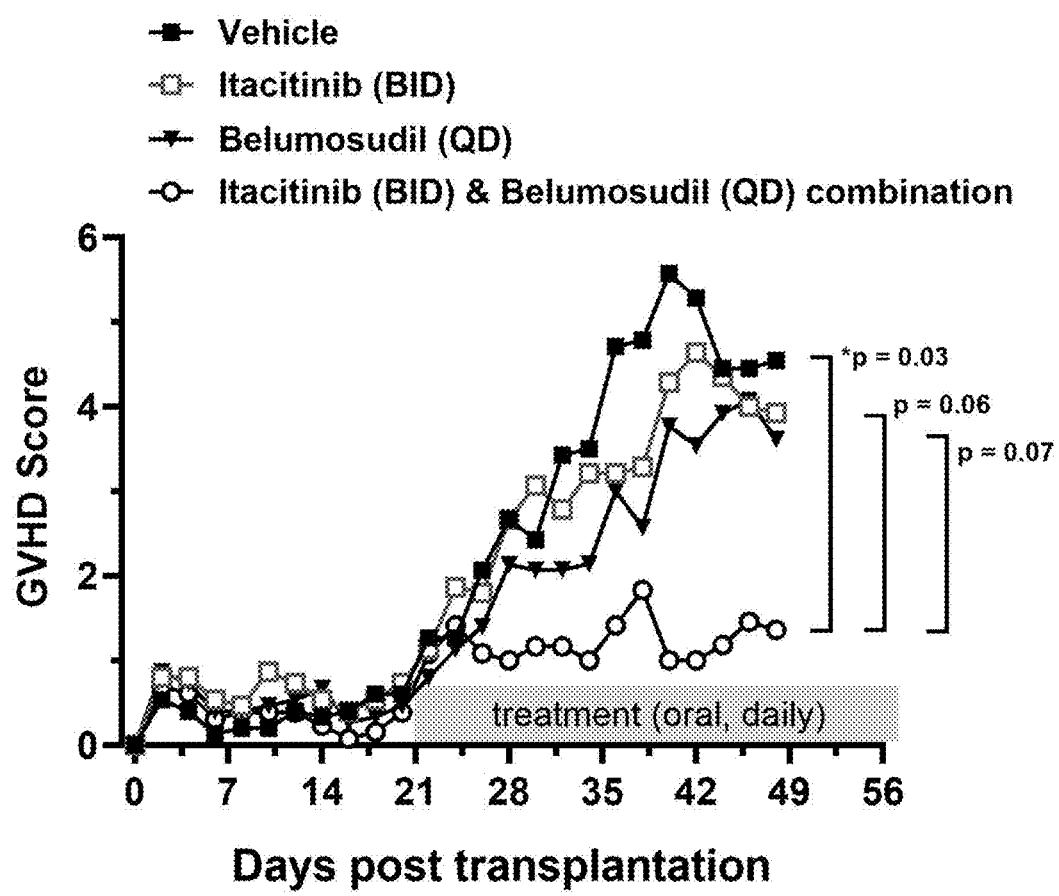
FIG. 1 shows graft versus host disease (GVHD) score in a murine model of sclerodermatous chronic GVHJD. Starting at day 21, mice were administered with vehicle, itacitinib, belumosudil, or itacitinib+belumosudil.

The present application provides a method of treating a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject, comprising administering to the subject:
  (i) a Janus kinase (JAK) inhibitor; and
  (ii) a Rho-associated protein kinase (ROCK) inhibitor.

In some embodiments, the present application provides a method of treating a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject:
  (i) a JAK1/2 inhibitor; and
  (ii) a ROCK inhibitor.

In some embodiments, the present application provides a method of a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject:
  (i) a selective JAK1 inhibitor; and
  (ii) a ROCK inhibitor.

In some embodiments, the present application provides a method of treating a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject:
  (i) a JAK inhibitor; and
  (ii) a ROCK2 inhibitor.

In some embodiments, the present application provides a method of treating a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject:
  (i) a JAK1/2 inhibitor; and
  (ii) a ROCK2 inhibitor.

In some embodiments, the present application provides a method of treating a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject:
  (i) a selective JAK1 inhibitor; and
  (ii) a ROCK2 inhibitor.

The methods described herein utilize JAK pathway inhibitors (e.g., JAK1/2 inhibitors, selective JAK1 inhibitors, and the like) and ROCK inhibitors (e.g., ROCK2 inhibitors), any of which can be in the form of a pharmaceutically acceptable salt.

JAK Pathway Inhibitors

I. JAK1/2 Inhibitors

In some embodiments, the methods provided herein utilize a JAK1/2 inhibitor.

In some embodiments, the JAK1/2 inhibitor is baricitinib, or a pharmaceutically acceptable salt thereof.

In some embodiments, the JAK1/2 inhibitor is ruxolitinib, or a pharmaceutically acceptable salt thereof (see e.g., U.S. Pat. No. 7,598,257, the disclosure of which is incorporated herein by reference in its entirety). In some embodiments, the salt is ruxolitinib phosphate (see e.g., U.S. Pat. No. 8,722,693, the disclosure of which is incorporated herein by reference in its entirety).

In some embodiments, the JAK1/2 inhibitor is ruxolitinib, or a pharmaceutically acceptable salt thereof, wherein one or more hydrogen atoms are replaced by deuterium atoms. In some embodiments, the JAK1/2 inhibitor is any of the compounds in U.S. Pat. No. 9,249,149 (which is incorporated herein by reference in its entirety), or a pharmaceutically acceptable salt thereof. In some embodiments, the JAK1/2 inhibitor is CTP-543 (Compound 111, having the structure below) or a pharmaceutically acceptable salt thereof,

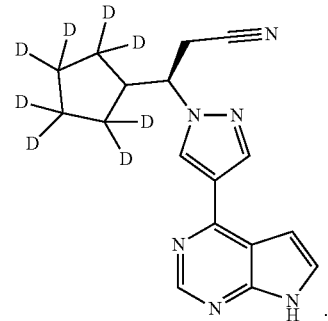 [SMILES: [2H]C1([2H])C([C@@H](CC#N)n2cc(-c3ncnc4[nH]ccc34)cn2)C([2H])([2H])C([2H])([2H])C1([2H])[2H]]

In some embodiments, the JAK1/2 inhibitor is a compound of Formula I:

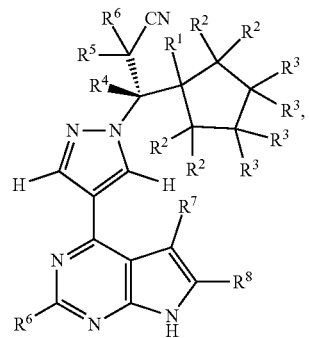

or a pharmaceutically acceptable salt thereof, wherein:

$R^1$ is selected from H and D;

each $R^2$ is independently selected from H and D, provided that each $R^2$ attached to a common carbon is the same;

each $R^3$ is independently selected from H and D, provided that each $R^3$ attached to a common carbon is the same;

$R^4$ is selected from H and D;

each $R^5$ is the same and is selected from H and D; and $R^6$, $R^7$, and $R^8$ are each independently selected from H and D; provided that when $R^1$ is H, each $R^2$ and each $R^3$ are H, $R^4$ is H, and each of $R^6$, $R^7$, and $R^8$ is H, then each $R^5$ is D.

In some embodiments, the JAK1/2 inhibitor is a compound of Formula I selected from the following compounds 100-130 in the table below (wherein $R^6$, $R^7$, and $R^8$ are each H), or a pharmaceutically acceptable salt thereof. In some embodiments, the inhibitor of JAK1 and/or JAK2 is a compound of Formula I selected from the following compounds 200-231 in the table below (wherein $R^6$, $R^7$, and $R^8$ are each D), or a pharmaceutically acceptable salt thereof.

| Compound | $R^1$ | Each $R^2$ | Each $R^3$ | $R^4$ | Each $R^5$ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK1/2 inhibitor is baricitinib, wherein one or more hydrogen atoms are replaced by deuterium atoms, or a pharmaceutically acceptable salt thereof. In some embodiments, the inhibitor of JAK1 and/or JAK2 is any of the compounds in U.S. Pat. No. 9,540,367 (which is incorporated herein by reference in its entirety), or a pharmaceutically acceptable salt thereof.

In some embodiments, the JAK1/2 inhibitor, or the pharmaceutically acceptable salt thereof, is oclacitinib, momelotinib, or brepocitinib, or a pharmaceutically acceptable salt thereof.

II. Selective JAK1 Inhibitors

In some embodiments, the methods utilized a JAK1 inhibitor. In some embodiments, the JAK1 inhibitor, or the pharmaceutically acceptable salt thereof, is upadacitinib, filgotinib, or abrocitinib, or a pharmaceutically acceptable salt thereof.

In some embodiments, the methods provided herein utilize selective JAK1 inhibitors. A selective JAK1 inhibitor is a compound that inhibits JAK1 activity preferentially over other Janus kinases. JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, et al., Autoimmunity Reviews, 8:538-42, 2009). Because IL-6 signals, at least in part, through JAK1, IL-6 can be indirectly through JAK1 inhibition, resulting in potential clinical benefit (Guschin, et al. *Embo J* 14:1421, 1995; Smolen, et al. Lancet 371:987, 2008). In other autoimmune diseases and cancers, elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases. Additionally, JAK1 inhibition is also being investigated in the role of CAR-T cell induced cytokine storm release (CRS) (NCT04071366).

The selective JAK1 inhibitors described herein, or pharmaceutically acceptable salts thereof, preferentially inhibit JAK1 over one or more of JAK2, JAK3, and TYK2. In some embodiments, the selective JAK1 inhibitors inhibit JAK1 preferentially over JAK2 (e.g., have a JAK2/JAK1 $IC_{50}$ ratio >1). In some embodiments, the selective JAK1 inhibitors or salts are about 10-fold more selective for JAK1 over JAK2. In some embodiments, the selective JAK1 inhibitors or salts are about 3-fold, about 5-fold, about 10-fold, about 15-fold, or about 20-fold more selective for JAK1 over JAK2 as calculated by measuring $IC_{50}$ at 1 mM ATP (e.g., see Example A).

In some embodiments, the selective JAK1 inhibitor is a compound of Table 1, or a pharmaceutically acceptable salt thereof. The $IC_{50}$ values obtained by the method of Example A at 1 mM ATP are shown in Table 1.

TABLE 1

| Comp. No. | Prep. | Name | Structure | JAK1 IC$_{50}$ (nM) | JAK2/ JAK1 |
|---|---|---|---|---|---|
| 1 | US 2011/ 0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 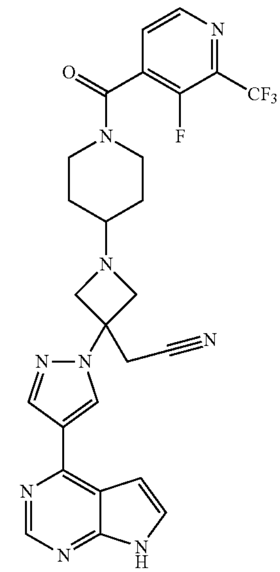 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 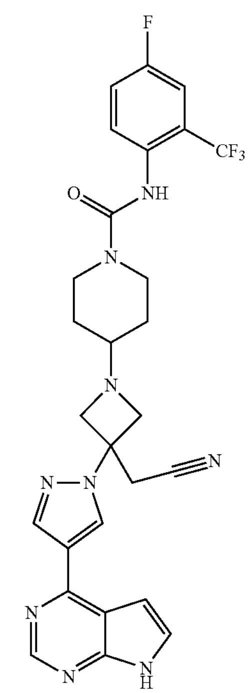 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 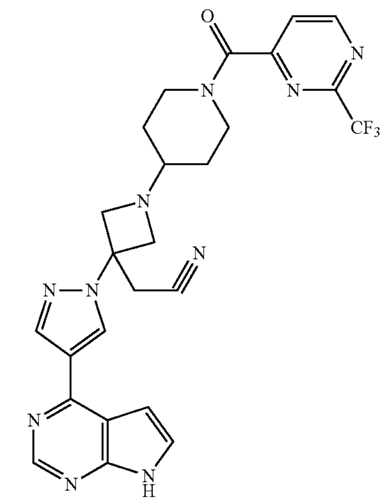 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 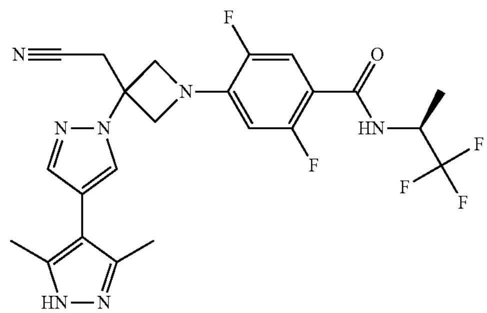 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 5 | US 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 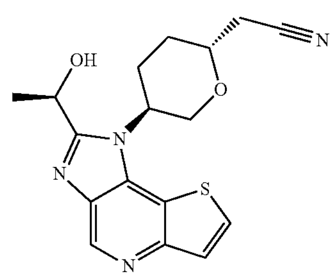 [SMILES: C[C@@H](O)c1nc2cnc3ccsc3c2n1[C@H]1CC[C@H](CC#N)OC1] | ++ | >10 |
| 6 | US 2010/ 0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 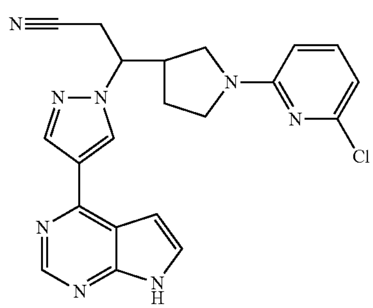 [SMILES: N#CCC(C1CCN(c2cccc(Cl)n2)C1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/ JAK1 |
|---|---|---|---|---|---|
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 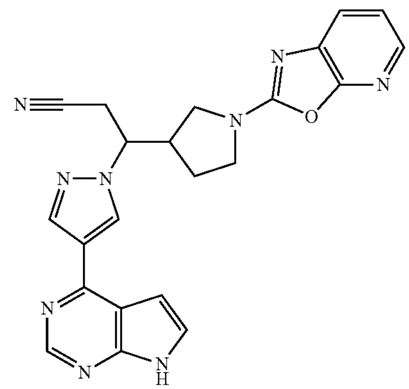 [SMILES: N#CCC(C1CCN(c2nc3cccnc3o2)C1)n1cc(-c2ncnc3[nH]ccc23)cn1] | + | >10 |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 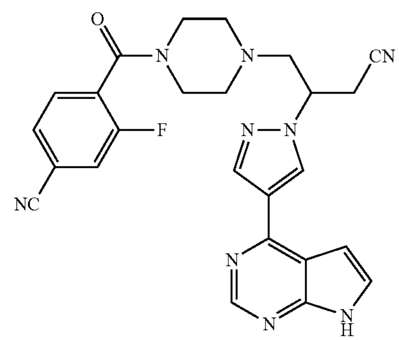 [SMILES: N#CCC(CN1CCN(C(=O)c2ccc(C#N)cc2F)CC1)n1cc(-c2ncnc3[nH]ccc23)cn1] | + | >10 |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 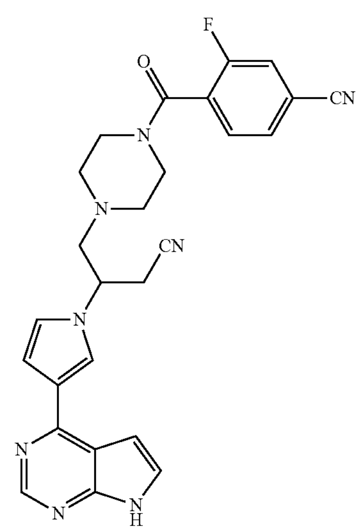 [SMILES: N#CCC(CN1CCN(C(=O)c2ccc(C#N)cc2F)CC1)n1ccc(-c2ncnc3[nH]ccc23)c1] | + | >10 |

TABLE 1-continued
| Comp. No. | Prep. | Name | Structure | JAK1 IC$_{50}$ (nM) | JAK2/ JAK1 |
|---|---|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl) pyrimidin-4-yl]carbonyl}piperazin-1-yl)cyclobutyl]acetonitrile | 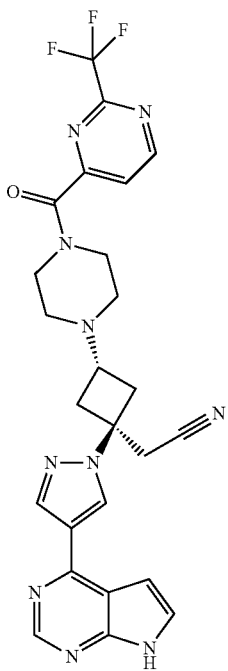 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 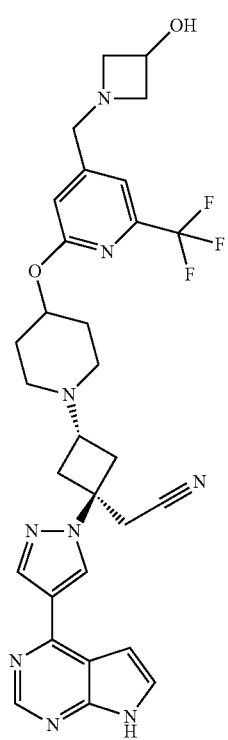 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 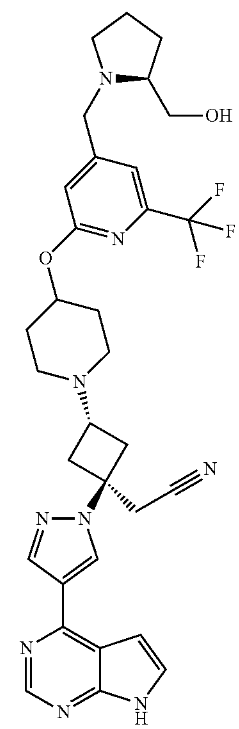 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 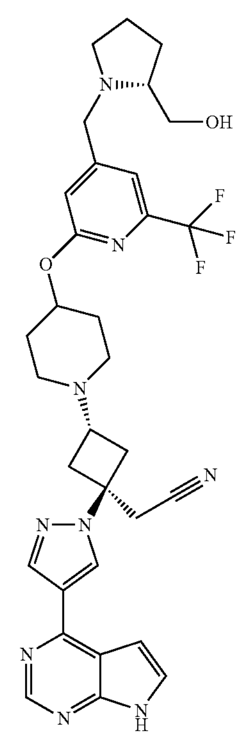 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 14 | US 2012/ 0149682 (Example 20)[b] | 4-(4-{3-[(dimethylamino) methyl]-5-fluorophenoxy}piperidin-1-yl)-3-[4-(7H-pyrrolo[2,3-d]pyrimidin-4-yl)-1H-pyrazol-1-yl]butanenitrile | 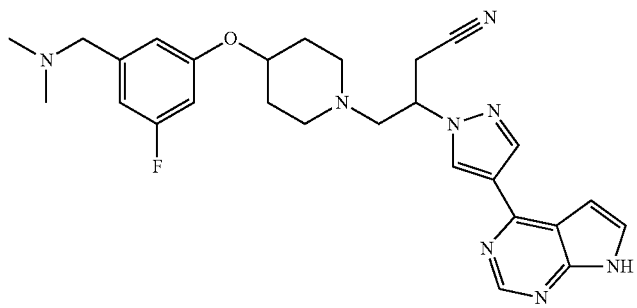 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 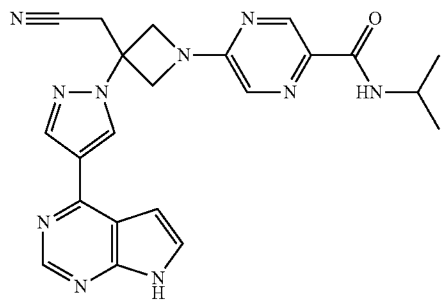 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 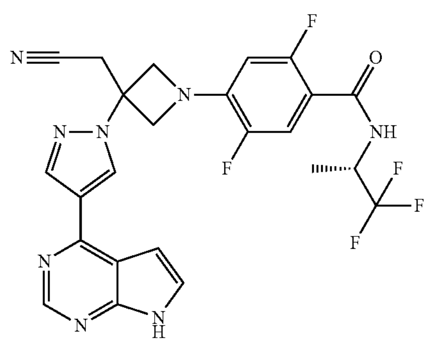 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 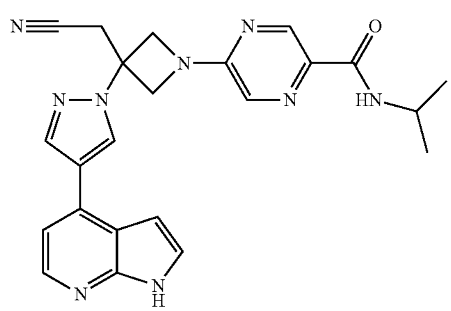 [SMILES: CC(C)NC(=O)c1cnc(N2CC(CC#N)(n3cc(-c4ccnc5[nH]ccc45)cn3)C2)cn1] | + | >10 |

TABLE 1-continued

| Comp. No. | Prep. | Name | Structure | JAK1 IC$_{50}$ (nM) | JAK2/JAK1 |
|---|---|---|---|---|---|
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 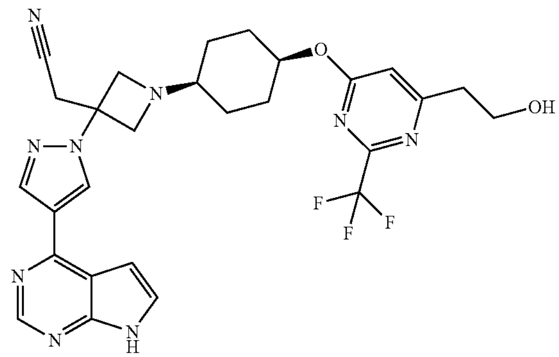 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 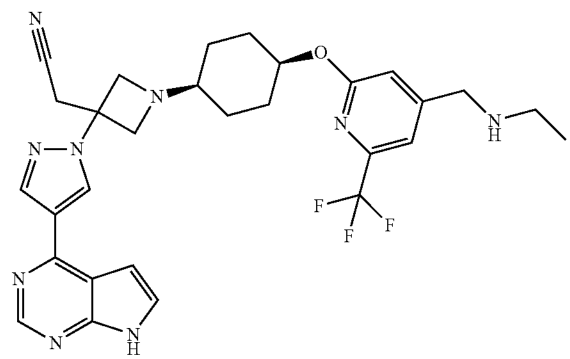 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 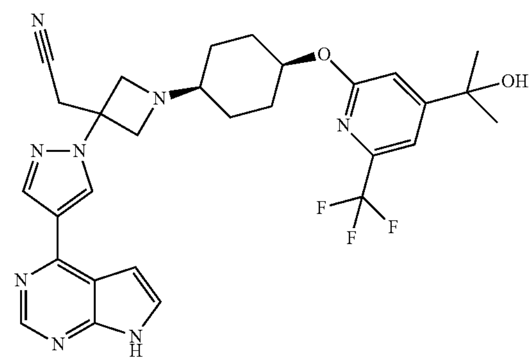 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 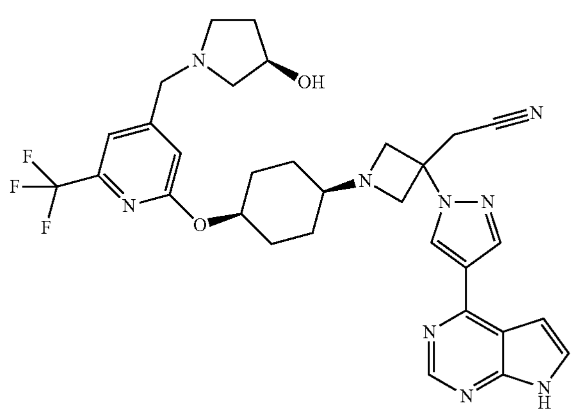 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 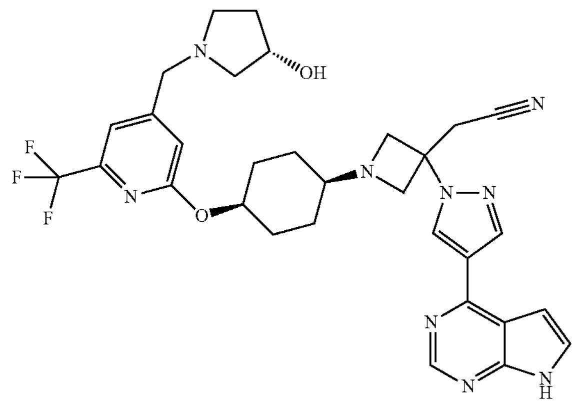 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 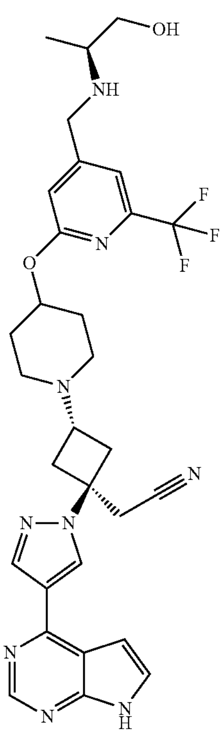 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 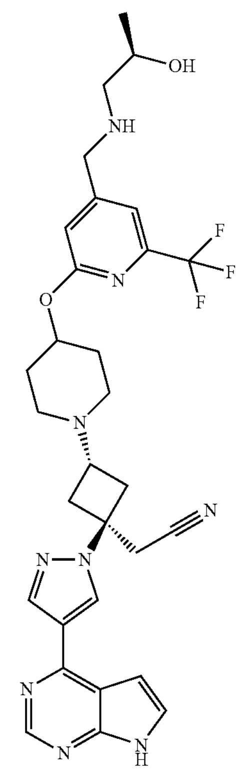 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 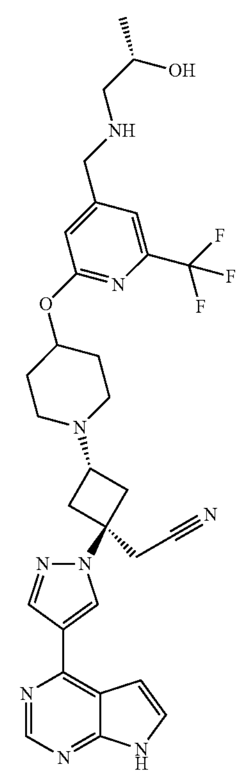 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/JAK1 |
|---|---|---|---|---|---|
| 26 | US 2014/0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 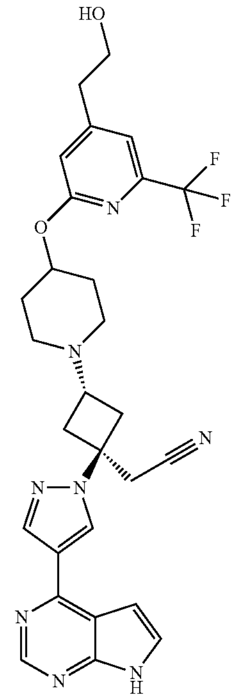 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+means <10 nM (see Example A for assay conditions)
++means ≤100 nM (see Example A for assay conditions)
+++means ≤300 nM (see Example A for assay conditions)
$^a$Data for enantiomer 1
$^b$Data for enantiomer 2

In some embodiments, the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the selective JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the selective JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the selective JAK1 inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the selective JAK1 inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 1 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. No. 2013/

0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, selective JAK1 inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the selective JAK1 inhibitor is a compound of Formula II.

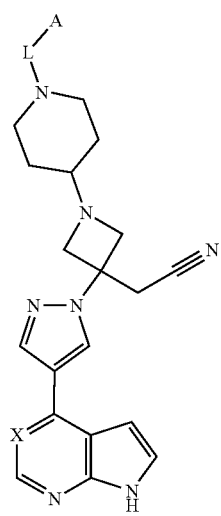

I or a pharmaceutically acceptable salt thereof, wherein:
X is N or CH;
L is C(=O) or C(=O)NH;
A is phenyl, pyridinyl, or pyrimidinyl each of which is optionally substituted with
1 or 2 independently selected $R^1$ groups; and
each $R^1$ is, independently, fluoro, or trifluoromethyl.

In some embodiments, the compound of Formula II is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula II is 4-{3-(cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula II is [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile, or a pharmaceutically acceptable salt thereof.

In some embodiments, the selective JAK1 inhibitor is a compound of Formula III:

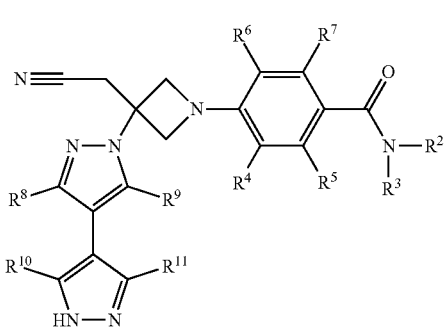

II or a pharmaceutically acceptable salt thereof, wherein:
$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;
$R^3$ is H or methyl;
$R^4$ is H, F, or Cl;
$R^5$ is H or F;
$R^6$ is H or F;
$R^7$ is H or F;
$R^1$ is H or methyl;
$R^9$ is H or methyl;
$R^{10}$ is H or methyl; and
$R^{11}$ is H or methyl.

In some embodiments, the compound of Formula III is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the selective JAK1 inhibitor is a compound of Formula IV:

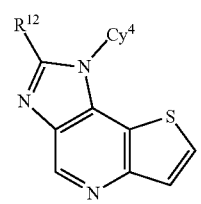

III or a pharmaceutically acceptable salt thereof, wherein:
$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and
$R^{12}$ is —$CH_2$—OH, —CH($CH_3$)—OH, or —$CH_2$—$NHSO_2CH_3$.

In some embodiments, the compound of Formula IV is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

ROCK Inhibitors

Examples of a Rho-associated coiled-coil containing protein kinase inhibitor include, but are not limited to, (R)-trans-N-(pyridin-4-yl)-4-(1-aminoethyl)cyclohexanecarboxamide, (R)-(+)-N-(1H-pyrrolo[2,3-b]pyridin-4-yl)-4-(1-aminoethyl)benzamide, or the like as disclosed in WO98/06433 and WO00/09162; a Rho-associated coiled-coil containing protein kinase inhibitor such as 1-(5-isoquinolinesulfonyl)homopiperazine, 1-(5-isoquinolinesulfonyl)-2-methylpiperazine, or the like as disclosed in WO97/23222; a Rho-associated coiled-coil containing protein kinase inhibitor such as (1-benzylpyrrolidin-3-yl)-(1H-indazol-5-yl)amine or the like as disclosed in WO01/56988; a Rho-associated coiled-coil containing protein kinase inhibitor such as (1-benzylpiperidin-4-yl)-(1H-indazol-5-yl)amine or the like as disclosed in WO02/100833; a Rho-associated coiled-coil containing protein kinase inhibitor such as N-[2-(4-fluorophenyl)-6,7-dimethoxy-4-quinazolinyl]-N-(1H-indazol-5-yl)amine or the like as disclosed in WO02/076976; a Rho-associated coiled-coil containing protein kinase inhibitor such as N-4-(1H-indazol-5-yl)-6,7-dimethoxy-N-2-pyridin-4-yl-quinazoline-2,4-diamine or the like as disclosed in WO02/076977; a Rho-associated coiled-coil containing protein kinase inhibitor such as 4-methyl-5-(2-methyl-[1,4]diazepane-1-sulfonyl)isoquinoline or the like as disclosed in WO99/64011; a Rho-associated coiled-coil containing protein kinase inhibitor such as (S)-(−)-1-(4-fluoro-5-isoquinolinesulfonyl)-2-methyl-1,4-homopiperazine or the like as disclosed in WO2006/068208; and a Rho-associated coiled-coil containing protein kinase inhibitor such as 4-(3-amino-1-(isoquinolin-6-ylamino)-1-oxopropan-2-yl) benzyl 2,4-dimethylbenzoate or the like as disclosed in WO2010/126626. The disclosures of International Patent Publication Nos.: WO98/06433, WO00/09162, WO97/23222, WO01/56988, WO02/100833, WO02/076976, WO02/076977, WO99/64011, WO2006/068208, and WO2010/126626 are each incorporated herein by reference in their entireties.

In some embodiments, the Rho-associated coiled-coil containing protein kinase inhibitor is ripasudil, or (S)-(−)-1-(4-fluoro-5-isoquinolinesulfonyl)-2-methyl-1,4-homopiperazine, or a pharmaceutically acceptable salt thereof.

In some embodiments, the Rho-associated coiled-coil containing protein kinase inhibitor is netarsudil, or [4-[(1S)-1-(aminomethyl)-2-(isoquinolin-6-ylamino)-2-oxoethyl]phenyl]methyl 2,4-dimethylbenzoate, or a pharmaceutically acceptable salt thereof.

In one embodiment, the Rho-associated coiled-coil containing protein kinase inhibitor is fasudil, or 5-(1,4-diazepane-1-sulfonyl)isoquinoline.

Additional Rho-associated coiled-coil containing protein kinase inhibitors include, but are not limited to, 4-substratated piperidone derivatives such as those described in U.S. Pat. Nos. 7,572,913 and 6,140,333 (e.g., BA-1049, BA-1041, BA-1042, BA-1043, BA-1044, BA-1050, and BA-1051), Y27632 [(R)-(+)-trans-4-(1-aminoethyl)-N-(4-pyridyl)cyclohexane-carboxamide as a dihydrochloride salt] which inactivates both ROCK1 and ROCK2 (see e.g., Ishizaki et al. Mol. Pharmacol. 2000, 57:976; and U.S. Pat. No. 4,997,834), Rho-associated coiled-coil containing protein kinase inhibitors such as those described in U.S. Pat. No. 9,815,820 (e.g., belumosudil or SLx-2119), HA-1077 (see e.g., Zhao et al. Neurol. Med. Chir., (2011), (Tokyo) 51:679-683) and azaindole-based inhibitors of rho kinase such as 6-chloro-N4-(3,5-difluoro-4-{(3-methyl-1H-pyrrolo{2,3-b}pyridine-4-yl)oxy}-phenyl) pyrimidine-2,4-diamine (azaindole) (see e.g., Kast et al. Brit. J. Pharmacol. 2007, 152:1070-1080). The disclosures of U.S. Pat. Nos. 4,997,834, 6,140,333, 7,572,913, and 9,815,820 are each incorporated herein by reference in their entireties.

In some embodiments, the Rho-associated coiled-coil containing protein kinase inhibitor is a Rho-associated coiled-coil kinase 2 inhibitor (ROCK2 inhibitor).

In some embodiments, the Rho-associated coiled-coil kinase 2 inhibitor is belumosudil (i.e., 2-(3-(4-((1H-indazol-5-yl)amino)quinazolin-2-yl)phenoxy)-N-isopropylacetamide), or a pharmaceutically acceptable salt thereof.

Methods of Use

In some embodiments, the disease or disorder is graft versus host disease. In some embodiments, the graft versus host disease is chronic graft versus host disease. In some embodiments, the graft versus host disease is sclerodermatous chronic graft versus host disease. In some embodiments, the graft versus host disease is acute graft versus host disease.

Itacitinib, a selective JAK1 pathway inhibitor, is currently under clinical investigation in the treatment of both acute and chronic post HSCT GVHD. Chronic GVHD (cGVHD) can affect any organ in the body with the most common being skin, liver, and intestines. Chronic GVHD can also affect the lungs and has a clinical presentation that is nearly identical to post-lung transplant BOS. The correlation between lung cGVHD and post-lung transplant BOS was first described in 1995, where clinical data and tissue were collected from 9 patients with lung cGVHD and post-lung transplant BOS. Both groups had similar signs and symptoms including progressive dyspnea and an irreversible obstructive pattern as well as similar outcomes and histology including diffuse inflammation leading to ectasia of the large bronchi (Philit et al., *Eur. Respir. J.* 1995, 8:551-558).

Lung cGVHD is initiated during the transplant process through the development of normal tissue damage that leads to a tissue damage response characterized by a release of cytokines, toll-like receptor agonists, neutrophils, platelets, and vascular inflammation (Cooke et al, *Biol. Blood Marrow Transplant* 2017, 23:211-234). CD4 and CD8 cells as well at Th17 cells are recruited to the site, however, due to thymic injury or dysfunction, there is impaired negative selection of these cells and autoreactive T-cell clones persist.

In addition, the requisite immunosuppression regimens used in cGVHD including CNIs lead to $T_{reg}$ depletion. Ultimately, the initial T-cell response leads to the activation of a variety of innate and adaptive immune cells including T, B, and NK cells as well as APCs to the site, leading to upregulation of proinflammatory cytokines TGFβ, PDGFα, TNFα, and IL17. This chronic inflammation and fibroblast recruitment ends with target organ collagen deposition and with continued dysfunction, fibrosis (Cooke et al, *Biol. Blood Marrow Transplant* 2017, 23:211-234).

Additionally, murine models have demonstrated that prophylactic and therapeutic dosing with itacitinib led to improvement in the GVHD score at either 60 mg/kg per day or 120 mg/kg per day indicating the clinical efficacy in an alloreactive mouse model. The JAK inhibitors ruxolitinib (a JAK1/2 inhibitor) and itacitinib have demonstrated clinical efficacy in acute GVHD (aGVHD); additionally ruxolitinib has produced clinical efficacy in chronic GVHD (cGVHD).

In some embodiments, the disease or disorder is chronic lung allograft dysfunction (CLAD). In some embodiments, the chronic lung allograft dysfunction (CLAD) is bronchiolitis obliterans syndrome (BOS).

The diagnosis of post-lung transplant BOS can be made clinically and can be defined by a persistent decline in lung function as measured by $FEV_1$. To make the diagnosis of post-lung transplant BOS, other causes of post-transplant decline including acute rejection, infection, native lung problems for single lung recipients, excessive recipient weight gain, anastomotic dysfunction, respiratory muscle dysfunction, effusion, or technical problems such as erroneous measurements due to device dysfunction as well as others can be excluded as the cause of lung graft dysfunction. (Meyer, K. C., et al. *Eur. Respir. J.* 2014; 44: 1479-1503). The BOS classification scheme, the accepted grading system for post-lung transplant BOS, can be based off of spirometric evaluation of a persistent decline in $FEV_1$ to ≤80% of baseline post-transplant baseline $FEV_1$. Baseline can be defined as the average of the two best $FEV_1$ (or $FEF_{25-75}\%$) values ≥3 weeks apart following functional recovery and stabilization post-lung transplantation. The most recent update provided below includes a new classification, Grade 0p, which was added to ensure early diagnosis of post-lung transplant BOS. (Meyer, K. C., et al. *Eur. Respir. J.* 2014; 44: 1479-1503). Table 1 was adapted from Meyer, K. C., et al. *Eur. Respir. J* 2014; 44: 1479-1503, which is hereby incorporated by reference in its entirety. $FEV_1$: Forced Expiratory Volume in 1 second; $FEF_{25-75\%}$: Forced Expiratory Flow at 25-75% of forced vital capacity

TABLE A

BOS Classification Scheme

| BOS Grade | Definition |
| --- | --- |
| 0 | $FEV_1 > 90\%$ and $FEF_{25-75\%} > 75\%$ |
| 0p | $FEV_1$ 81-90% and $FEF_{25-75\%} \leq 75\%$ |
| 1 | $FEV_1$ 66-80% |
| 2 | $FEV_1$ 51-65% |
| 3 | $FEV_1 \leq 50\%$ |

Many of the same biologic principles related to cGVHD are inherent in post-lung transplant BOS. The main difference being that in cGVHD the immune response is aberrant and leads to transplanted stem cells attacking host tissue whereas in post lung transplant BOS, the immune response is physiologically normal, although it still leads to poor outcomes for patients. In post-lung transplant BOS, the inciting event for alloreactive acute inflammation phase is clear, namely, an allogeneic lung graft implant; however, it should be noted that similar to cGVHD, patients with events leading to graft tissue injury including an acute rejection episode following transplant, CMV infection as well as other tissue damaging phenomena such as GERD and cold ischemic time are more likely to develop post-lung transplant BOS (Meyer, K. C., et al. *Eur. Respir. J.* 2014; 44: 1479-1503). Thymic dysfunction seen with cGVHD is not relevant in post-lung transplant BOS as alloreactive T cells would not be negatively selected. Importantly, however, roles for an early CD4, CD8, and Th17 cell infiltrate, as well as subsequent recruitment of B cell, NK cell, and APCs are all well documented in post-lung transplant BOS, even if these are physiologically appropriate (Boehler and Estenne, *Eur. Respir. J.* 2003, 22:1007-1018; Gupta et al., *Am. J. Respir. Cell Mol. Biol.* 2017, 56:708-715; Fukami et al., *Am. J. Transplant,* 2012, 12:867-876; Hodge et al, *J. Heart Lung Transplant,* 2012, 31:888-895, Leonard et al., *Am. J. Respir. Crit. Care Med.* 2000, 161:1349-1354). Similar to cGVHD, maintenance immunosuppression regimens use CNIs leading to $T_{reg}$ depletion and inhibition (Meyer, K. C., et al. *Eur. Respir. J.* 2014; 44: 1479-1503). Finally, each of the known cytokines, including TGFβ, PDGFα, TNFα, and IL-17 as well as cellular mediators of aberrant tissue repair have a documented presence in post-lung transplant BOS.

There is no standard of care or consensus treatment algorithm for BOS therapy, and there are few high quality randomized trials which demonstrate clear benefit in BOS patients (Meyer, K. C., et al. *Eur. Respir. J.* 2014; 44: 1479-1503).

Of note, 4 out of 5 patients in a study with lung cGVHD had $FEV_1$ responses as defined by an increase in $FEV_1$ of ≥10%. In addition, a study that examined the use of ruxolitinib in 5 pediatric patients (4 evaluable) with lung cGVHD demonstrated 2 responses with 1 patient having an increase in $FEV_1$ of 9%. Four out of five patients were able to wean steroids completely and the final patient was able to decrease the steroid requirement by >50% (Schoettler et al, *Bone Marrow Transplantation,* 2019, 54:1158-1160. In addition to ruxolitinib, itacitinib has demonstrated significant clinical activity in patients with aGVHD. A recent study evaluated the safety and efficacy of 2 doses of itacitinib, 200 mg QD and 300 mg QD, in patients with treatment naïve or steroid refractory aGVHD.

In some embodiments, the subject is a lung transplant recipient (e.g., a single lung transplant recipient or a double lung transplant recipient).

In some embodiments, the subject is a double lung transplant recipient.

In some embodiments, the subject suffers from Grade 0, Grade 0p, Grade 1, Grade 2, or Grade 3 bronchiolitis obliterans syndrome as determined by International Society for Heart and Lung Transplantation (ISHLT) criteria.

In some embodiments, the subject suffers from Grade 0p, Grade 1, Grade 2 or Grade 3 bronchiolitis obliterans syndrome as determined by International Society for Heart and Lung Transplantation (ISHLT) criteria.

In some embodiments, the subject suffers from Grade 1 or Grade 2 bronchiolitis obliterans syndrome as determined by International Society for Heart and Lung Transplantation (ISHLT) criteria.

In some embodiments, the subject has a fractional decrease in $FEV_1$ to less than or about 50%, 55%, 60%, 65%, 70%, 75%, 80%, 85%, 90%, or 95% of post-transplant baseline $FEV_1$. These values can be used to define a range, such as from about 50% to about 75%.

In some embodiments, the subject has a $FEF_{25}$-75% value of more than, less than or about 50%, 55%, 60%, 65%, 70%, 75%, 80%, 85%, 90%, or 95%. These values can be used to define a range, such as from about 60% to about 80%.

In some embodiments, the subject suffers from Grade 0 bronchiolitis obliterans syndrome, wherein Grade 0 bronchiolitis obliterans syndrome is defined as a fractional decrease in $FEV_1$ to less than 100%, but greater than 90% of post-transplant baseline $FEV_1$ and/or baseline $FEF_{25}$-75% of greater than 75% of post-transplant baseline.

In some embodiments, the subject suffers from Grade 0p bronchiolitis obliterans syndrome, wherein Grade 0p bronchiolitis obliterans syndrome is defined as a fractional decrease in $FEV_1$ to 81-90% of post-transplant baseline $FEV_1$ and/or baseline $FEF_{25}$-75% of less than or equal to 75% of post-transplant baseline.

In some embodiments, the subject suffers from Grade 1 bronchiolitis obliterans syndrome, wherein Grade 1 bronchiolitis obliterans syndrome is defined as a fractional decrease in $FEV_1$ to 66-80% of post-transplant baseline $FEV_1$.

In some embodiments, the subject suffers from Grade 2 bronchiolitis obliterans syndrome, wherein Grade 2 bronchiolitis obliterans syndrome is defined as a fractional decrease in $FEV_1$ to 51-65% of post-transplant baseline $FEV_1$.

In some embodiments, the subject suffers from Grade 3 bronchiolitis obliterans syndrome, wherein Grade 3 bronchiolitis obliterans syndrome is defined as a fractional decrease in $FEV_1$ to less than or equal to 50% of post-transplant baseline $FEV_1$.

In some embodiments, treating bronchiolitis obliterans syndrome comprises about, or greater than about, a 5%, 10%, 15%, 20%, 25%, 30%, 35%, 40%, 45% or 50% increase in $FEV_1$ at about 4 weeks, 8 weeks, 12 weeks, 3 months, 4 months, 5 months or 6 month following the first administration of the JAK inhibitor and ROCK inhibitor, as described herein.

In some embodiments, treating bronchiolitis obliterans syndrome comprises about, or greater than about, a 5%, 10%, 15%, 20%, 25%, 30%, 35%, 40%, 45% or 50% increase in $FEV_1$ at about 4 weeks, 8 weeks, 12 weeks, 3 months, 4 months, 5 months or 6 month following the first administration of the JAK inhibitor and ROCK inhibitor, as described herein.

In some embodiments, treating bronchiolitis obliterans syndrome comprises about, or greater than about, a 10% increase in $FEV_1$ at about 12 weeks following the first administration of the JAK inhibitor and ROCK inhibitor, as described herein.

In some embodiments, treating bronchiolitis obliterans syndrome comprises about a 10% or greater increase in $FEV_1$ at twelve weeks following the first administration of the JAK inhibitor and ROCK inhibitor, as described herein.

In some embodiments, the present application provides a method of reducing the risk of bronchiolitis obliterans syndrome in a subject, said method comprising administering to the subject a JAK inhibitor and a ROCK inhibitor, as described herein.

In some embodiments, the present application provides a method of reducing the risk of lung re-transplantation in a subject, said method comprising administering to the subject a JAK inhibitor and a ROCK inhibitor, as described herein.

In some embodiments, the present application provides a method of improving the $FEV_1$ in a subject with bronchiolitis obliterans syndrome, the method comprising administering to the subject a JAK inhibitor and a ROCK inhibitor, as described herein.

In some embodiments, the present application provides a method of improving the quality of life in a subject with bronchiolitis obliterans syndrome, the method comprising administering to the subject a JAK inhibitor and a ROCK inhibitor, as described herein.

In some embodiments, the present application provides a method of reducing death, reducing progressive bronchiolar ectasia, reducing organ failure, reducing decline in lung function, increasing recovery and stabilization post-lung transplantation, decreasing hospitalization, decreasing health care utilization, and/or reducing the risk of re-transplantation, as well as other potential benefits as provided herein, in a subject, the method comprising administering to the subject a JAK inhibitor and a ROCK inhibitor, as described herein.

In some embodiments, the present application provides a method of reducing the risk of hospitalization in a subject, said method comprising administering to said subject a JAK inhibitor and a ROCK inhibitor, as described herein, wherein said subject is (a) diagnosed with bronchiolitis obliterans syndrome; (b) has had a lung transplantation within 1 to 5 years prior to administering the JAK inhibitor and a ROCK inhibitor, and (c) does not have a decrease in $FEV_1$ attributable to a cause other than bronchiolitis obliterans syndrome.

In some embodiments, the present application provides a method for treating non-transplant related bronchiolitis obliterans syndrome in a subject, comprising administering to the subject a JAK inhibitor and a ROCK inhibitor, as described herein.

In some embodiments, the disease or disorder is restrictive allograft syndrome (RAS).

In some embodiments, the disease or disorder is systemic sclerosis (scleroderma).

Dosing and Administration

In some embodiments, the JAK inhibitor is administered to the subject in a daily amount of from about 1 mg to about 2000 mg, about 10 mg to about 2000 mg, or about 100 mg to about 2000 mg.

In some embodiments, the JAK inhibitor is administered to the subject in a daily amount of from about 50 mg to about 1200 mg on a free base basis. Accordingly, in some embodiments, the JAK inhibitor is administered to the subject in a daily amount of about 50 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg. about 975 mg, about 1000 mg, about 1025 mg, about 1050 mg, about 1075 mg, about 1100 mg, about 1125 mg, about 1150 mg, about 1175 mg, or about 1200 mg on a free base basis.

In some embodiments, the JAK inhibitor is administered to the subject in a daily amount of from about 200 mg to about 1200 mg on a free base basis. In some embodiments, the JAK inhibitor is administered to the subject in a daily amount of from about 200 mg to about 1200 mg on a free base basis on days 1-28 in a 28 day cycle of treatment. A daily amount of from about 200 mg to about 1200 mg can be administered twice daily, e.g., by separate doses of from about 100 mg to about 600 mg.

In some embodiments, the JAK inhibitor is administered to the subject in a daily amount of from about 100 mg to about 600 mg on a free base basis.

In some embodiments, the JAK inhibitor is administered to the subject in a daily amount of from about 100 mg to about 600 mg on a free base basis on days 1-28 in a 28 day cycle of treatment.

In some embodiments the JAK inhibitor is administered to the subject once daily.

In some embodiments, the JAK inhibitor is administered to the subject twice daily.

In some embodiments, the dose of the JAK inhibitor is administered to the subject as one or more sustained-release dosage forms. Sustained-release dosage forms of the JAK inhibitor {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof (Table 1, Compound 1) can be found in U.S. Pat. Nos. 9,655,854 and 10,561,616, which are incorporated herein by reference.

In some embodiments, the dose of the JAK inhibitor is administered as one or more immediate release dosage forms.

In some embodiments, the ROCK inhibitor is administered to the subject in a daily amount of from about 1 mg to about 2000 mg, about 10 mg to about 2000 mg, or about 100 mg to about 2000 mg.

In some embodiments, the ROCK inhibitor is administered to the subject in a daily amount of from about 50 mg to about 1200 mg on a free base basis. Accordingly, in some embodiments, the ROCK inhibitor is administered to the subject in a daily amount of about 50 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg. about 975 mg, about 1000 mg, about 1025 mg, about 1050 mg, about 1075 mg, about 1100 mg, about 1125 mg, about 1150 mg, about 1175 mg, or about 1200 mg on a free base basis.

In some embodiments, the ROCK inhibitor is administered to the subject in an amount of from about 100 mg/kg to about 300 mg/kg on a free base basis.

In some embodiments, the ROCK inhibitor is administered to the subject in an amount of from about 100 mg/kg to about 200 mg/kg on a free base basis.

In some embodiments, the ROCK inhibitor is administered to the subject in an amount of about 100 mg/kg on a free base basis.

In some embodiments, the ROCK inhibitor is administered to the subject in an amount of about 150 mg/kg on a free base basis.

In some embodiments, the ROCK inhibitor is administered to the subject in an amount of about 200 mg/kg on a free base basis.

In some embodiments, the ROCK inhibitor is administered to the subject in an amount of about 250 mg/kg on a free base basis.

In some embodiments, the ROCK inhibitor is administered to the subject in an amount of about 300 mg/kg on a free base basis.

In some embodiments the ROCK inhibitor is administered to the subject once daily.

In some embodiments, the ROCK inhibitor is administered to the subject twice daily.

In some embodiments, the dose of the ROCK inhibitor is administered to the subject as one or more sustained-release dosage forms.

In some embodiments, the dose of the ROCK inhibitor is administered as one or more immediate release dosage forms.

In some embodiments, the JAK inhibitor and the ROCK inhibitor are administered simultaneously. In some embodiments, the JAK inhibitor and the ROCK inhibitor are administered sequentially. In some embodiments, the JAK inhibitor and the ROCK inhibitor are each administered once daily. In some embodiments, the JAK inhibitor and the ROCK inhibitor are each administered orally, once daily. In some embodiments, the JAK inhibitor and the ROCK inhibitor are each administered twice daily. In some embodiments, the JAK inhibitor and the ROCK inhibitor are each administered orally, twice daily.

In some embodiments, administration of the JAK inhibitor and ROCK inhibitor provides an improvement in one or more symptoms of the disease or disorder provided herein.

In some embodiments, administration of the JAK inhibitor and ROCK inhibitor provides an improvement in one or more symptoms of GVHD (e.g., as measured by the GVHD score) in the subject, compared to the one or more symptoms prior to administration of the JAK inhibitor and ROCK inhibitor.

In some embodiments, administration of the JAK inhibitor and ROCK inhibitor reduces or stops progression of one or more symptoms of the disease or disorder provided herein.

In some embodiments, administration of the JAK inhibitor and ROCK inhibitor reduces or stops progression of one or more symptoms of GVHD (e.g., as measured by the GVHD score) in the subject, compared to the one or more symptoms prior to administration of the JAK inhibitor and ROCK inhibitor.

In some embodiments, administration of the JAK inhibitor and ROCK inhibitor provides a reduction in the GVHD score of the subject compared to the GVHD score of the subject prior to administration of the JAK inhibitor and ROCK inhibitor. For example, in some embodiments administration of the JAK inhibitor and ROCK inhibitor provides a reduction in the GVHD score of the subject from 4 to 3, from 4 to 2, from 4 to 1, from 4 to 0, from 3 to 2, from 3 to 1, from 3 to 0, from 2 to 1, from 2 to 0, or from 1 to 0. An assessment of sclerodermatous GVHD score is provided herein in Example 1, Table 3.

In some embodiments, administration of the JAK inhibitor and ROCK inhibitor provides an improvement in one or more of weight loss of the subject, posture of the subject, activity of the subject, hair texture of the subject, and skin integrity of the subject, as measured by the GVHD score, compared to the weight loss of the subject, posture of the subject, activity of the subject, hair texture of the subject, and skin integrity of the subject prior to administration of the JAK inhibitor and ROCK inhibitor.

In some embodiments, administration of the JAK inhibitor and ROCK inhibitor provides an improvement in weight loss of the subject as measured by the GVHD score, compared to the weight loss of the subject as measured by the GVHD score, prior to administration of the JAK inhibitor and ROCK inhibitor. For example, in a subject exhibiting >15% weight loss prior to administration of the JAK inhibitor and ROCK inhibitor (Grade 4 as measured by the GVHD score), then administration of the JAK inhibitor and ROCK inhibitor may reduce the weight loss of the subject to between 10% and 15% (Grade 3 as measured by the GVHD score), between 5% and 10% (Grade 2 as measured by the GVHD score), between 0% and 5% (Grade 1 as measured by the GVHD score), or no weight loss (Grade 0 as measured by the GVHD score).

In some embodiments, administration of the JAK inhibitor and ROCK inhibitor provides an improvement in the posture of the subject as measured by the GVHD score, compared to the posture of the subject as measured by the GVHD score, prior to administration of the JAK inhibitor and ROCK inhibitor. For example, in a subject exhibiting severe hunched posture prior to administration of the JAK inhibitor and ROCK inhibitor (Grade 3 as measured by the GVHD score), then administration of the JAK inhibitor and ROCK inhibitor may improve the posture of the subject to a moderate hunched posture (Grade 2 as measured by the GVHD score), a mild hunched posture (Grade 1 as measured by the GVHD score), or a normal posture (Grade 0 as measured by the GVHD score).

In some embodiments, administration of the JAK inhibitor and ROCK inhibitor provides an improvement in the activity of the subject as measured by the GVHD score, compared to the activity of the subject as measured by the GVHD score, prior to administration of the JAK inhibitor and ROCK inhibitor. For example, in a subject exhibiting immobility prior to administration of the JAK inhibitor and ROCK inhibitor (Grade 3 as measured by the GVHD score), then administration of the JAK inhibitor and ROCK inhibitor may improve the activity of the subject to a slowed gait with refusal to move when touched (Grade 2 as measured by the GVHD score), a slowed gait (Grade 1 as measured by the GVHD score), or a normal activity (Grade 0 as measured by the GVHD score).

In some embodiments, administration of the JAK inhibitor and ROCK inhibitor provides an improvement in the hair texture of the subject as measured by the GVHD score, compared to the hair texture of the subject as measured by the GVHD score, prior to administration of the JAK inhibitor and ROCK inhibitor. For example, in a subject exhibiting complete hair loss or >1 cm$^2$ area involved hair loss prior to administration of the JAK inhibitor and ROCK inhibitor (Grade 4 as measured by the GVHD score), then administration of the JAK inhibitor and ROCK inhibitor may improve the hair texture of the subject to hair loss in a single area >1 cm$^2$ (Grade 3 as measured by the GVHD score), hair loss in a single area <1 cm$^2$ (Grade 2 as measured by the GVHD score), ruffled hair with small amount of hair loss (Grade 1 as measured by the GVHD score), or normal hair texture (Grade 0 as measured by the GVHD score).

In some embodiments, administration of the JAK inhibitor and ROCK inhibitor provides an improvement skin integrity of the subject as measured by the GVHD score, compared to the hair texture of the subject as measured by the GVHD score, prior to administration of the JAK inhibitor and ROCK inhibitor. For example, in a subject exhibiting scabbing or bleeding with multiple lesions prior to administration of the JAK inhibitor and ROCK inhibitor (Grade 4 as measured by the GVHD score), then administration of the JAK inhibitor and ROCK inhibitor may improve the skin integrity of the subject to scabbing or bleeding with a single lesion (Grade 3 as measured by the GVHD score), skin flaking/peeling with a single lesion (Grade 2 as measured by the GVHD score), a red/irritated skin lesion (Grade 1 as measured by the GVHD score), or normal skin integrity (Grade 0 as measured by the GVHD score).

In some embodiments, the present application provides a method of treating a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject about 150 mg to about 250 mg {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, on a free base basis; 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject about 150 mg to about 250 mg {1-{1-[3-fluoro-2-(trifluoromethyl)isonicotinoyl]piperidin-4-yl}-3-[4-(7H-pyrrolo[2, 3-d]pyrimidin-4-yl)-1H-pyrazol-1-yl]azetidin-3-yl}acetonitrile adipic acid salt; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject about 200 mg {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, on a free base basis; 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject about 200 mg {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and about 100 mg/kg to about 200 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating sclerodermatous chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and about 100 mg/kg to about 200 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating sclerodermatous chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and about 150 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating sclerodermatous chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and 150 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating sclerodermatous chronic graft versus host disease in a subject, comprising administering to the subject about 150 mg to about 250 mg {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and about 100 mg/kg to about 200 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating sclerodermatous chronic graft versus host disease in a subject, comprising administering to the subject about 150 mg to about 250 mg {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and about 100 mg/kg to about 200 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating sclerodermatous chronic graft versus host disease in a subject, comprising administering to the subject about 200 mg {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and about 150 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating sclerodermatous chronic graft versus host disease in a subject, comprising administering to the subject about 200 mg {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and 150 mg/kg 2-(3-(4-((1H-indazol-5-yl)amino)quinazolin-2-yl)phenoxy)-N-isopropylacetamide, or a pharmaceutically acceptable salt thereof, on a free base basis.

In some embodiments, the present application provides a method of treating a disease or disorder selected from graft versus host disease (GVHD), restrictive allograft syndrome (RAS), chronic lung allograft dysfunction (CLAD) (e.g., bronchiolitis obliterans syndrome (BOS)), and systemic sclerosis (scleroderma) in a subject, comprising administering to the subject (R)-3-(4-(7H-pyrrolo[2,3-d]pyrimidin-4-yl)-1H-pyrazol-1-yl)-3-cyclopentylpropanenitrile, or a pharmaceutically acceptable salt thereof, and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating graft versus host disease in a subject, comprising administering to the subject (R)-3-(4-(7H-pyrrolo[2,3-d]pyrimidin-4-yl)-1H-pyrazol-1-yl)-3-cyclopentylpropanenitrile, or a pharmaceutically acceptable salt thereof; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating graft versus host disease in a subject, comprising administering to the subject (R)-3-(4-(7H-pyrrolo[2,3-d]pyrimidin-4-yl)-1H-pyrazol-1-yl)-3-cyclopentylpropanenitrile phosphate; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating chronic graft versus host disease in a subject, comprising administering to the subject (R)-3-(4-(7H-pyrrolo[2,3-d]pyrimidin-4-yl)-1H-pyrazol-1-yl)-3-cyclopentylpropanenitrile, or a pharmaceutically acceptable salt thereof, and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating chronic graft versus host disease in a subject, comprising administering to the subject (R)-3-(4-(7H-pyrrolo[2,3-d]pyrimidin-4-yl)-1H-pyrazol-1-yl)-3-cyclopentylpropanenitrile phosphate; and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject (R)-3-(4-(7H-pyrrolo[2,3-d]pyrimidin-4-yl)-1H-pyrazol-1-yl)-3-cyclopentylpropanenitrile, or a pharmaceutically acceptable salt thereof, and 2-(3-(4-((1H-indazol-5-yl)amino)quinazolin-2-yl)phenoxy)-N-isopropylacetamide, or a pharmaceutically acceptable salt thereof.

In some embodiments, the present application provides a method of treating sclerodermatous chronic graft versus host disease in a subject, comprising administering to the subject (R)-3-(4-(7H-pyrrolo[2,3-d]pyrimidin-4-yl)-1H-pyrazol-1-yl)-3-cyclopentylpropanenitrile phosphate; and 2-(3-(4-((1H-indazol-5-yl)amino)quinazolin-2-yl)phenoxy)-N-isopropylacetamide, or a pharmaceutically acceptable salt thereof.

The embodiments described herein are intended to be combined in any suitable combination as if the embodiments are multiply dependent claims (e.g., the embodiments related to the JAK inhibitors and doses of the same, the embodiments related to the ROCK2 inhibitors and doses of the same, the embodiments related to any salt forms of the compounds disclosed herein, and the embodiments related to compositions and/or administration can be combined in any combination). All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as 0-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 2 can be optionally substituted with deuterium atoms, such as —$CD_3$ being substituted for —$CH_3$).

The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The terms "individual," "patient," and "subject" are used interchangeably, and refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds provided herein are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, one or more of the compounds of the disclosure or a pharmaceutically acceptable salt thereof (e.g., one or more of the JAK pathway inhibitors, and/or one or more ROCK inhibitors, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 2000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, about 950 to about 1000 mg, about 1000 mg to about 1100 mg, about 1100 mg to about 1200 mg, about 1200 mg to about 1300 mg, about 1300 mg to about 1400 mg, about 1400 mg to about 1500 mg, about 1500 mg to about 1600 mg, about 1600 mg to about 1700 mg, about 1700 mg to about 1800 mg, about 1800 mg to about 1900 mg, or about 1900 mg to about 2000 mg of the active ingredient(s).

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Kits

The present application also includes pharmaceutical kits useful, which include one or more containers containing a pharmaceutical composition comprising a therapeutically effective amount of the compound, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example A. In Vitro JAK Kinase Assay

Selective JAK1 inhibitors that can be used in combination with a ROCK inhibitor as described herein are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2, or JAK3 was assayed by measuring the phosphorylation of a biotinylated peptide. The phosphorylated peptide was detected by homogenous time resolved fluorescence (HTRF). $IC_{50}$s of compounds are measured for each kinase in the 40 μL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 μL 45 mM EDTA, 300 nM SA-APC, 6 nM Eu-Py20 in assay buffer (Perkin Elmer, Boston, MA). Binding to the Europium labeled antibody takes place for 40 minutes and HTRF signal was measured on a Fusion plate reader (Perkin Elmer, Boston, MA). The compounds in Table 1 were tested in this assay and shown to have the $IC_{50}$ values in Table 1.

Example B. Cellular Assays

JAK inhibitors that can be used in combination with ROCK inhibitors as described herein are tested for inhibitory activity of JAK targets according to at least one of the following cellular assays.

To study the effect of the compounds on T-cell activation, mouse splenocytes are plated at $2 \times 10^6$ cells per well (24 well plate format) in RPMI 1640, 10% FBS, 100 U/ml penicillin, 100 μg/ml streptomycin, 0.05 mm beta-mercaptoethanol and activated with CD3/CD28 beads (Gibco, Waltham, MA). Compounds are added to the cells in DMSO/media (final concentration 0.2% DMSO) and incubated for 72 hours at 37° C., 5% $CO_2$. The effect of the compound/compounds is assessed by quantifying cytokines levels using a multi-spot assay system, pro-inflammatory panel 1 (for IFN-γ, IL-1β, IL-2, IL-4, IL-5, IL-6, KC/GRO, IL-10, IL-1p70, and TNFα, Meso Scale Diagnostics [MSD], Rockville, Maryland).

Additionally, the compound effect on T-cell activation can be measured by a mixed lymphocyte reaction (MLR) assay. Dendritic cells are generated by culturing isolated bone marrow cells from femurs and tibiae from BALB/c mice in RPMI 1640, 10% FBS, 100 U/ml penicillin, 100 μg/ml streptomycin and 25 ng/ml granulocyte macrophage colony-stimulating factor (GM-CSF) and incubated at 37° C., 5% $CO_2$ ($3 \times 10^6$ cells per well, 6 well plate format). Allogenic responder C57BL/6 splenocytes are labelled with carboxyfluorescein succinimidyl ester (CFSE) dye and added to the culture 7 days later, along with compounds. The effect of the compounds on T-cell activation is assessed by measuring cytokine secretion (MSD, Rockville, Maryland) as well as T-cell proliferation by CFSE dilution by flow cytometry.

To study the effect of the compounds on macrophages, mouse splenocytes are plated at $3 \times 10^6$ cells per well (6 well plate format) in RPMI 1640, 10% FBS, 100 U/ml penicillin, 100 μg/ml streptomycin and 50 ng/ml macrophage colony-stimulating factor (M-CSF) and incubated at 37° C., 5% $CO_2$. On day 6, cells are treated with compound. On day 7, macrophages are activated with 5 ng/mL lipopolysaccharide (LPS) and 24 hours later the effect of the compound is assessed by measuring cytokines from supernatants (MSD, Rockville, Maryland).

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 μg/ml streptomycin) at a density of $2 \times 10^6$ cells/ml at 37° C. for up to 2 days. For IL-2 stimulated cell proliferation analysis, T-cells are first treated with Phytohemagglutinin (PHA) at a final concentration of 10 μg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, WI).

Example 1. Combination Treatment Using JAK1 Inhibitor and ROCK2 Inhibitor in a Mouse Model of Sclerodermatous Chronic Graft Versus Host Disease (GvHD)

The effects of therapeutic dosing of a selective JAK1 inhibitor (itacitinib), a ROCK2 inhibitor (belumosudil), and a combination the selective JAK1 inhibitor and ROCK2 inhibitor (itacitinib+belumosudil) combination were tested in a murine model of sclerodermatous chronic GVHD.

Sclerodermatous chronic GVHD was induced in C57Bl/6 mice using a single acute dose of 8.5 Gy of total body irradiation on Day −1. On Day 0, recipient mice were given an intravenous injection of a combination of splenocytes and bone marrow cells from donor LP/J mice. Starting at day 21, animals were dosed with vehicle, itacitinib, belumosudil, or the combination of both itacitinib and belumosudil (P.O., B.I.D, see Table 2). All animals were monitored on a daily basis to record weight change, survival and GVHD score (see Table 3). On days 33, 36, 39, 42 and 45 all animals were photographed under isoflurane anesthesia to assess disease severity.

TABLE 3

| Criteria | Grade 0 | Grade 1 | Grade 2 | Grade 3 | Grade 4 |
|---|---|---|---|---|---|
| Weight Loss | no weight loss | >0% <5% | >5% <10% | >10% <15% | >15% |
| Posture | Normal | Mild hunched posture | Moderate hunched posture | Severe hunched posture | — |
| Activity | Normal | Slowed gait | Slowed gait; refusal to move when touched | Immobility when touched | — |
| Fur Texture | Normal | Ruffled hair; small amount of hair loss | Hair loss in a single area <1 cm$^2$ | Hair loss in a single area >1 cm$^2$ | Complete hair loss or >1 cm$^2$ area involved |
| Skin Integrity | Normal | Red/irritated skin lesion | Skin flaking/peeling; single lesion | Scabbing or bleeding; single lesion | Scabbing or bleeding; multiple lesions |

Figure 2:
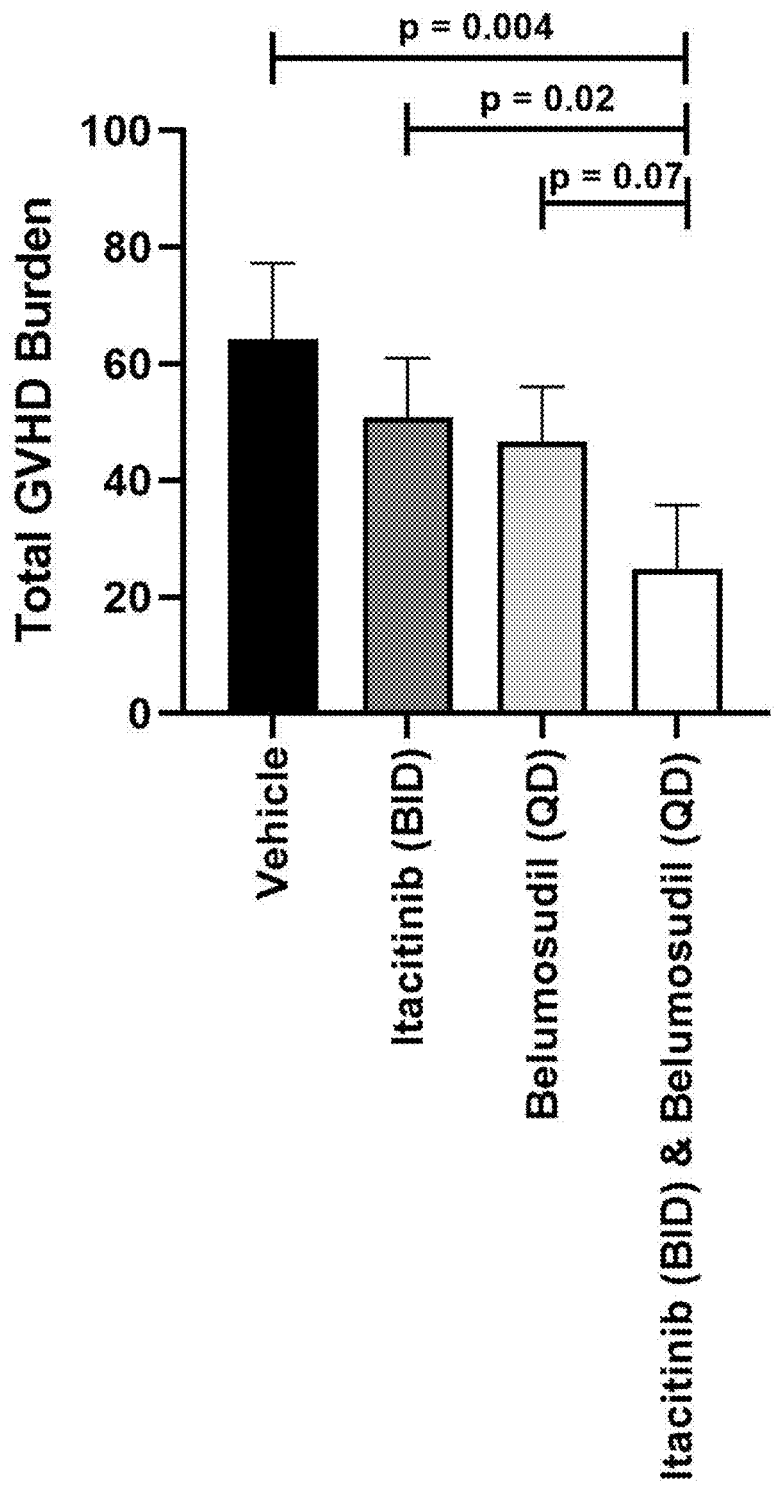
FIG. 2 shows total GVHD burden in a murine model of sclerodermatous chronic GVHJD after administration of vehicle, itacitinib, belumosudil, or itacitinib+belumosudil.

Treatment with single agent itacitinib or belumosudil provided reduction in GVHD scores when compared to vehicle-treated animals (see FIG. 1). Combination therapy with itacitinib and belumosudil provided significant reduction in GVHD scores when compared to vehicle-treated animals (see FIG. 1). By AUC analysis, combination therapy-treated animals displayed significantly lower GVHD scores than vehicle, itacitinib-treated animals and belumosudil-treated animals (see FIG. 2). These results shows that itacitinib+belumosudil combination treatment has potential synergistic efficacy in a mouse model of sclerodermatous chronic GVHD.

Example 2. Combination Treatment Using JAK1/2 Inhibitor and ROCK2 Inhibitor in a Mouse Model of Sclerodermatous Chronic Graft Versus Host Disease (GVHD)

The effects of therapeutic dosing of a JAK1/2 inhibitor (ruxolitinib), a ROCK2 inhibitor (belumosudil), and a combination of the JAK1/2 inhibitor and ROCK2 inhibitor (ruxolitinib+belumosudil) combination were tested in a murine model of sclerodermatous chronic GVHD.

Sclerodermatous chronic GVHD was induced in C57Bl/6 mice using a single acute dose of 8.5 Gy of total body irradiation on Day −1. On Day 0, recipient mice were given an intravenous injection of a combination of splenocytes and bone marrow cells from donor LP/J mice. Starting at day 21,

TABLE 2

| Group | No. Animals | TBI (Day −1) | Cell Transfer (Day 0) | Treatment | Schedule | Photo | Sacrifice & Collections (Day 56) |
|---|---|---|---|---|---|---|---|
| 1 | 15 | 8.5 Gy | $4 \times 10^6$ splenocytes $1 \times 10^7$ bone | vehicle | BID, PO d21-56 | Days 33, 36, 39, 42, | skin, lung, blood |
| 2 | 15 | 8.5 Gy | $4 \times 10^6$ splenocytes $1 \times 10^7$ bone | Itacitinib 120 mg/kg | BID, PO d21-56 | Days 33, 36, 39, 42, | skin, lung, blood |
| 3 | 15 | 8.5 Gy | $4 \times 10^6$ splenocytes $1 \times 10^7$ bone | Belumosudil 150 mg/kg | QD, PO d21-56 | Days 33, 36, 39, 42, | skin, lung, blood |
| 4 | 15 | 8.5 Gy | $4 \times 10^6$ splenocytes $1 \times 10^7$ bone | Itacitinib + Belumosudil | BID, PO + QD, PO d21-56 | Days 33, 36, 39, 42, | skin, lung, blood | animals were dosed with vehicle, ruxolitinib, belumosudil, or the combination of both ruxolitinib and belumosudil (P.O., B.I.D, see Table 4). All animals were monitored on a daily basis to record weight change, survival and GVHD score (see Table 5). On days 33, 36, 39, 42 and 45 all animals were photographed under isoflurane anesthesia to assess disease severity.

TABLE 4

| Group | No. Animals | TBI (Day −1) | Cell Transfer (Day 0) | Treatment | Schedule | Photo | Sacrifice & Collections (Day 56) |
|---|---|---|---|---|---|---|---|
| 1 | 15 | 8.5 Gy | 4 × 10$^6$ splenocytes 1 × 10$^7$ bone | vehicle | BID, PO d21-56 | Days 33, 36, 39, 42, | skin, lung, blood |
| 2 | 15 | 8.5 Gy | 4 × 10$^6$ splenocytes 1 × 10$^7$ bone | Ruxolitinib 60 mg/kg | BID, PO d21-56 | Days 33, 36, 39, 42, | skin, lung, blood |
| 3 | 15 | 8.5 Gy | 4 × 10$^6$ splenocytes 1 × 10$^7$ bone | Belumosudil 150 mg/kg | QD, PO d21-56 | Days 33, 36, 39, 42, | skin, lung, blood |
| 4 | 15 | 8.5 Gy | 4 × 10$^6$ splenocytes 1 × 10$^7$ bone | Ruxolitinib + Belumosudil | BID, PO + QD, PO d21-56 | Days 33, 36, 39, 42, | skin, lung, blood |

TABLE 5

| Criteria | Grade 0 | Grade 1 | Grade 2 | Grade 3 | Grade 4 |
|---|---|---|---|---|---|
| Weight Loss | no weight loss | >0% <5% | >5% <10% | >10% <15% | >15% |
| Posture | Normal | Mild hunched posture | Moderate hunched posture | Severe hunched posture | — |
| Activity | Normal | Slowed gait | Slowed gait; refusal to move when touched | Immobility when touched | — |
| Fur Texture | Normal | Ruffled hair; small amount of hair loss | Hair loss in a single area <1 cm$^2$ | Hair loss in a single area >1 cm$^2$ | Complete hair loss or >1 cm$^2$ area involved |
| Skin Integrity | Normal | Red/ irritated skin lesion | Skin flaking/ peeling; single lesion | Scabbing or bleeding; single lesion | Scabbing or bleeding; multiple lesions |

Figure 3:
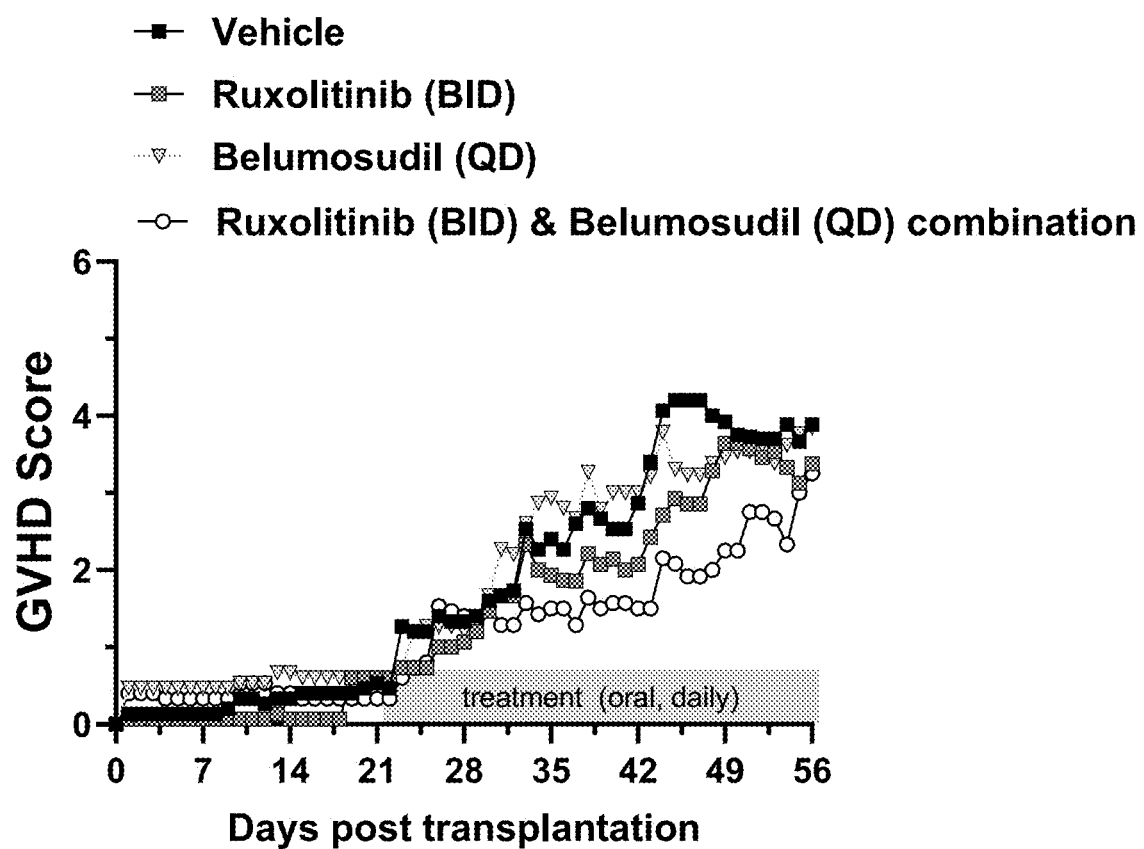
FIG. 3 shows graft versus host disease (GVHD) score in a murine model of sclerodermatous chronic GVHD. Starting at day 21, mice were administered with vehicle, ruxolitinib, belumosudil, or ruxolitinib+belumosudil.
Figure 4:
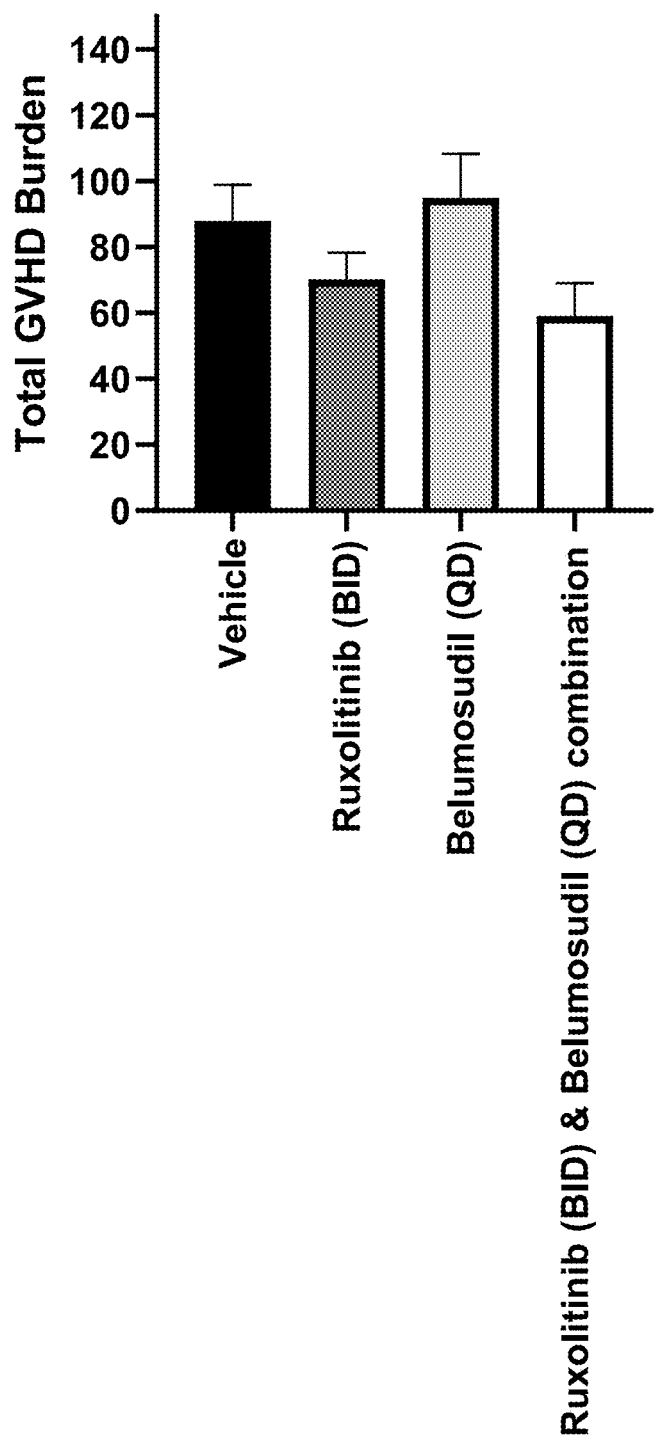
FIG. 4 shows total GVHD burden in a murine model of sclerodermatous chronic GVHD after administration of vehicle, ruxolitinib, belumosudil, or ruxolitinib+belumosudil.

Treatment with single agent ruxolitinib provided numerical reduction in GVHD scores when compared to vehicle-treated animals while single agent belumosudil provided no benefit (see FIG. 3). By AUC analysis, combination therapy-treated animals displayed lower GVHD scores than vehicle, ruxolitinib-treated animals, and belumosudil-treated animals (see FIG. 4). Combination therapy resulted in numerically lower AUC disease burden compared to either ruxolitinib or belumosudil single agent therapy.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a disease or disorder selected from graft versus host disease, restrictive allograft syndrome, chronic lung allograft dysfunction, and systemic sclerosis in a subject, comprising administering to the subject:

a JAK inhibitor; and (ii) a ROCK inhibitor;

wherein the JAK inhibitor is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; and wherein the ROCK inhibitor is 2-(3-(4-((1H-indazol-5-yl)amino)quinazolin-2-yl)phenoxy)-N-isopropylacetamide, or a pharmaceutically acceptable salt thereof.

2. The method of claim 1, wherein the JAK inhibitor is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

3. The method of claim 1, wherein the JAK inhibitor is administered to the subject in a dose of about 100 mg to about 300 mg.

4. The method of claim 1, wherein the JAK inhibitor is administered to the subject in a dose of about 200 mg.

5. The method of claim 1, wherein ROCK inhibitor is administered to the subject is a dose of about 200 mg/kg to about 300 mg/kg.

6. The method of claim 1, wherein ROCK inhibitor is administered to the subject is a dose of about 200 mg/kg.

7. The method of claim 1, wherein the JAK inhibitor is administered to the subject once daily.

8. The method of claim 1, wherein the JAK inhibitor is administered to the subject orally, once daily.

9. The method of claim 1, wherein the JAK inhibitor is administered to the subject twice daily.

10. The method of claim 1, wherein the JAK inhibitor is administered to the subject orally, twice daily.

11. The method of claim 1, wherein the ROCK inhibitor is administered to the subject once daily.

12. The method of claim 1, wherein the ROCK inhibitor is administered to the subject orally, once daily.

13. The method of claim 1, wherein the ROCK inhibitor is administered to the subject twice daily.

14. The method of claim 1, wherein the ROCK inhibitor is administered to the subject orally, twice daily.

15. The method of claim 1, wherein the JAK inhibitor and the ROCK inhibitor are each administered to the subject orally, twice daily.

16. The method of claim 1, wherein the disease or disorder is graft versus host disease.

17. The method of claim 16, wherein the graft versus host disease is chronic graft versus host disease.

18. The method of claim 16, wherein the graft versus host disease is sclerodermatous chronic graft versus host disease.

19. The method of claim 1, wherein administration of the JAK inhibitor and ROCK inhibitor to the subject provides a reduction in the GVHD score of the subject compared to the GVHD score of the subject prior to administration of the JAK inhibitor and ROCK inhibitor.

20. A method of treating sclerodermatous chronic graft versus host disease in a subject, comprising administering to the subject {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt; and 2-(3-(4-(((1H-indazol-5-yl)amino)quinazolin-2-yl) phenoxy)-N-isopropylacetamide, or a pharmaceutically acceptable salt thereof.

21. The method of claim 1, wherein the JAK inhibitor and ROCK inhibitor are administered to simultaneously.

22. The method of claim 1, wherein the JAK inhibitor and ROCK inhibitor are administered to sequentially.

\* \* \* \* \*

UNITED STATES PATENT AND TRADEMARK OFFICE
CERTIFICATE OF CORRECTION

| | | |
|---|---|---|
| PATENT NO. | : 11,918,581 B2 | Page 1 of 1 |
| APPLICATION NO. | : 17/571844 | |
| DATED | : March 5, 2024 | |
| INVENTOR(S) | : Michael Peel and Paul Smith | |

It is certified that error appears in the above-identified patent and that said Letters Patent is hereby corrected as shown below:

In the Claims

Column 52, Line 3, Claim 1 – before "a JAK" insert -- (i) --.

Signed and Sealed this
Thirtieth Day of April, 2024

*Katherine Kelly Vidal*

Katherine Kelly Vidal
*Director of the United States Patent and Trademark Office*